United States Patent [19]

Saville

[11] Patent Number: Plant 6,214

[45] Date of Patent: Jul. 5, 1988

[54] ROSE PLANT

[75] Inventor: F. Harmon Saville, Rowley, Mass.

[73] Assignee: Nor'East Miniature Roses, Inc., Rowley, Mass.

[21] Appl. No.: 884,754

[22] Filed: Jul. 11, 1986

[51] Int. Cl.[4] ..... A01H 5/00

[52] U.S. Cl. ..... Plt./10

[58] Field of Search ..... Plt./10

*Primary Examiner*—Robert E. Bagwill

*Attorney, Agent, or Firm*—Vincent G. Gioia

[57] ABSTRACT

A new miniature rose variety of unusual cinnamon coloring having good substance.

1 Drawing Sheet

The present invention relates to a new and distinct variety of rose plant of the miniature rose class, which was originated by my crossing as seed parent the rose known as "Zorina" (U.S. Plant Pat. No. 2,321) and as pollen parent an unpatented, unnamed seedling of my creation. The varietal denomination of this new variety is "Savacin".

Among the novel characteristics possessed by this new variety which distinguish it from its parents and all other varieties of which I am aware are its attractive and unusual cinnamon colored flowers of good substance that open well through development and aging. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "178A" is plate 178A of The Royal Horticultural Society Colour Chart.

Parentage: Seedling.

*Seed parent.*—"Zorina".

*Pollen parent.*—Unnamed, unpatented seedling.

Class: Miniature.

The following observations are made of specimens grown under glass in Essex County, Mass., during the month of March.

FLOWER

Blooming habit: Recurrent.

A. Bud:

(1) *Size.*—Medium.

(2) *Form.*—Pointed.

(3) *Color.*—When sepals fall, indication of color is near 178A to B with pronounced yellow coloring at base.

(4) *Sepals.*—Longer than bud, lightly foliated, relatively smooth.

(5) *Peduncle.*—Length — about 1⅛ inch. Aspect — straight. Strength — erect. Color — near 176C.

B. Bloom:

(1) *Size.*—Average size when fully expanded — about 1⅝ inch.

(2) *Borne.*—Primarily singly.

(3) *Form.*—High centered at first, becoming flat, outer petals roll under slightly at edges.

(4) *Petalage.*—Number of petals under normal conditions — about 18 to 20.

(5) *Color.*—Bud coloring begins with greyed-red near 178A to 178B with pronounced yellow petal base at point of attachment. As buds open, flower coloring becomes greyed-orange ("Cinnamon") colored, with distinctive petal veining and washing with light tones. Outer petal tonality appears near 171A. Yellow base is most visible before flower is fully open. Overall general appearance from a distance is a cinnamon color.

C. Petals:

(1) *Texture.*—Good substance.

(2) *Appearance.*—Inside — velvety, outside — satiny.

(3) *Form.*—Broad, fan shaped with slight point at apex.

(4) *Arrangement.*—Regularly arranged, imbricated (5) *Petaloids in center.*—Few to none.

(6) *Persistence.*—Drop off cleanly.

(7) *Fragrance.*—Slight.

(8) *Lasting Quality.*—Average on plant and as cut flower.

REPRODUCTIVE ORGANS

A. Stamens, filaments and anthers:

(1) *Arrangement.*—Regularly arranged around styles.

(2) *Color.*—Near 188C.

B. Pollen:

*Color.*—None observed.

C. Styles: Even length, medium.

D. Stigmas:

*Color.*—Near 160C.

E. Hips: None observed.

PLANT

A. Form: Upright.

B. Growth: Vigorous, uniform branching

*Height attained.*—About 14 to 18 inches.

C. Foliage: Compound 5 to 7 leaflets.

(1) *Size.*—Medium.

(2) *Quantity.*—Abundant.

(3) *Color.*—New foliage: Upper side — near to 138A. Under side — near to 137D. Old foliage: Upper side — near 137B. Under side — near 138B.

(4) *Shape.*—Oval, pointed.

(5) *Texture.*—Upper side is glossy and under side is matte.

(6) *Edge.*—Serrated.

(7) *Serration.*—Serrate.

(8) *Leaf stem.*—Color — near 184B. Under side — near 199D.

(9) *Stipules.*—Medium, slightly bearded.

(10) *Resistance to disease.*—Blackspot — average. Mildew — average. Rust — average.

D. Wood:

(1) *New wood.*—Color — near 176A. Bark — smooth.

(2) *Old wood.*—Color — near 147B. Bark — smooth.

E. Thorns:

(1) *Thorns.*—Quantity (main stalk) — ordinary. On laterals from stalk — few. Form — long, thin, straight, pointed. Length — medium. Color — near 176A. Position — irregular.

(2) *Prickles.*—None.

F. Winter hardiness: Requires ordinary protection in extreme climates.

I claim:

1. A new and distinct variety of rose plant of the miniature rose class, substantially as shown and described, characterized particularly by unusually attractive cinnamon colored flowers of good substance that open well through development and aging.

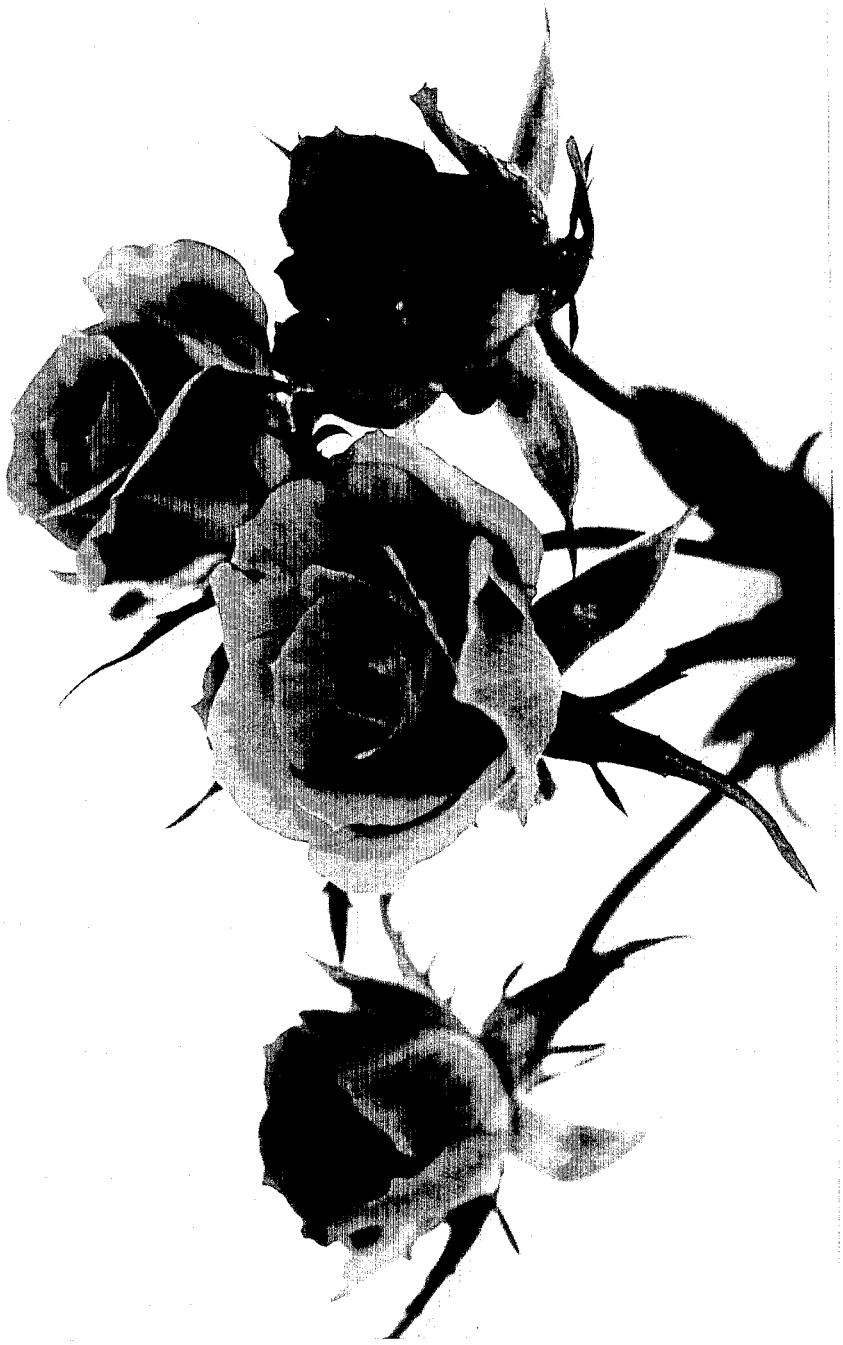

* * * * *